United States Patent [19]

Emmelmann

[11] Patent Number: 6,046,242
[45] Date of Patent: Apr. 4, 2000

[54] USE OF ARYL-SUBSTITUTED CYCLOBUTYLALKYLAMINES FOR TREATING URINARY INCONTINENCE

[75] Inventor: Gerhard Emmelmann, Oftersheim, Germany

[73] Assignee: BASF Aktiengesellschaft, Ludwigshafen, Germany

[21] Appl. No.: 09/201,309

[22] Filed: Nov. 27, 1998

[51] Int. Cl.[7] .................................................. A61K 31/135
[52] U.S. Cl. ............................................................ 514/646
[58] Field of Search ...................... 514/650, 449, 514/549, 646, 656, 657; 554/57, 54, 52; 564/123; 558/432

[56] References Cited

U.S. PATENT DOCUMENTS 4,746,680  5/1988  Jeffery et al . ......................... 514/646
5,436,272  7/1995  Scheinbaum ............................ 514/646

FOREIGN PATENT DOCUMENTS 9638134  12/1996  WIPO .

OTHER PUBLICATIONS

Sepracor Press Release "Sepracor Announces Phase II Results of (S)–Oxybutynin Proof–of–Concept Trial", Nov. 11, 1998.

*Primary Examiner*—William R. A. Jarvis
*Assistant Examiner*—Vickie Kim
*Attorney, Agent, or Firm*—Keil & Weinkauf

[57] ABSTRACT

This invention discloses Ary-substituted cyclobutylalkylamine compounds of formula I

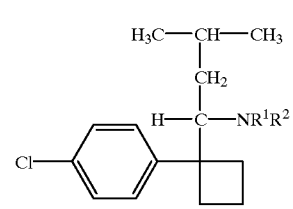

in which $R^1$ and $R^2$ are as defined in the specification, and their use in treating incontinence in humans.

15 Claims, No Drawings

USE OF ARYL-SUBSTITUTED CYCLOBUTYLALKYLAMINES FOR TREATING URINARY INCONTINENCE

BACKGROUND OF THE INVENTION

The invention relates to the use of aryl-substituted cyclobutylalkylamines for treating urinary incontinence.

DE 32 12 682 discloses aryl-substituted cyclobutylalkylamines. The compounds disclosed therein are employed as antidepressants. WO 90/06110 discloses the use of N,N-dimethyl-1-1[1-(4-chlorophenyl)cyclobutyl]-3-methylbutylamine hydrochloride for treating obesity. Enantiomers of aryl-substituted cyclobutylalkylamines and their preparation are described in WO 96/38134.

BRIEF SUMMARY OF THE INVENTION

The present invention relates to the use of aryl-substituted cyclobutylalkylanines of the formula I

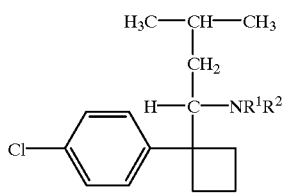

wherein $R^1$ and $R^2$ are identical or different and are hydrogen or methyl, and their pharmaceutically suitable salts, for treating urinary incontinence.

The compounds used according to the invention have this advantage of very good bioavailability and show a favorable spectrum of side effects.

DETAILED DESCRIPTION OF THE INVENTION

Compounds of the formula I can be in the form of salts with pharmaceutically suitable acids. Salts of inorganic and organic acids are suitable.

Examples of salts of these types comprise sulfates, hydrochlorides, hydrobromides, nitrates, phosphates, naleates, acetates, citrates, lactates, benzoates, arylsulfonates. alkylsulfonates, especially methane-, ethane-, propane and butanesulfonates, fumarates, gluconates, tartrates, succinates, tosylates and salts with acidic amiro acids, such as aspartic acid or glutamic acid. Hydrochlorides, acetates, phosphates and tosylates are preferred. Most preferred are the hydrochlorides.

Compounds of the formula I contain an asymmetric carbon atom and can exist in two enantiomeric forms. The present invention includes both the enantiomeric forms and the mixtures thereof. The dextrorotatory compounds have proven to he particularly preferred.

The compounds of the formula I are used in pharmaceutical preparations which contain a therapeutically effective amount of a compound of the formula I together with a pharmaceutically suitable diluent or vehicle. For therapeutic use, the active compound can be administered orally, rectally, or tonically, preferably orally. Accordingly, the therapeutic preparations of the present invention may have the form of any of the known pharmaceutical preparations for oral, rectal, or topical administration. Pharmaceutically suitable vehicles suitable for use in preparations of these types are known to the person skilled in the pharmaceutical art. The preparations of the invention may contain from 5 to 90% by weight of the active compound. The preparations according to the invention are usually produced in single-dose form.

Preparations for oral administration are the preferred preparations of the invention, and these are the known pharmaceutical forms for an administration of this type, for example tablets, film coated tablets, bilayer tablets, film coated bilayer tablets, capsules, syrups and aqueous or oily suspensions with acute or delayed release profile. The vehicles used to produce these preparations are those known to the person skilled in the pharmaceutical art. Tablets can be produced by mixing the active compound with an inert diluent such as calcium phosphate in the presence of dispersing or dissolving agents, for example corn starch and lubricants, for example magnesium stearates, and tabletting the mixture by known processes. The tablets can be formulated in a manner known to the skilled worker in order to ensure uniform release of the compounds of the present invention. Tablets of this type can, if required, be provided by known processes with coatings which dissolve only in the intestine, for example by use of cellulose acetate phthalate. It is possible in a similar way for capsules, for example hard or soft gelatin capsules which contain the active compound with or without added vehicle, to be produced by conventional processes and, if required, be provided in a known manner with coatings which dissolve only in the intestine. The tablets and capsules may each suitably contain from 5 to 20 mg of active compound. The tablets can also be produced by extrusion processes, with or without subsequent shaping. Extrusion processes of this type are known in the art (eg. EP 240 904, EP 240 906 and EP 358 105).

Other preparations for oral administration comprise, for example, aqueous suspensions which contain the active compound in an aqueous medium in the presence of a non-toxic suspending agent such as sodium carboxymethylcellulose, and oily suspensions which contain a compound of the present invention in a suitable vegetable oil, for example in arachis oil.

Preparations of the present invention suitable for rectal administration are the known pharmaceutical forms for an administration of this type, for example suppositories with cocoa butter or polyethylene glycol bases.

Preparations with compounds of the formula I suitable for parenteral administration are the known pharmaceutical forms for an administration of this type, for example sterile suspensions in aqueous or oily media, or sterile solutions in a suitable solvent.

Preparations for topical administration may contain a base in which the Pharmacologically active compounds of the present invention are dispersed so that the compounds are kept in contact with the skin in order to administer the compounds transdermally. The active compounds can be dispersed as selected in a pharmaceutically suitable cream or ointment base.

It may be advantageous for some formulations to use the compounds of the present invention in the form of very small particles, for example those obtained by milling in an air jet mill.

The active compound can, if required, be combined with other suitable pharmacologically active ingredients in the preparations of the present invention.

The pharmaceutical preparations which contain a therapeutically effective amount of a compound of the formula I can be employed for treating urinary incontinence. The amount of the compound of the formula I administered per patient and day for such a treatment depends or various factors, e.g. the age and weight of the patient. In addition the dose depends on the severity of the case. It is normally in the range from 5 to 100, preferably 5 to 50 and most preferably 5 to 30 mg administered in one or more doses, preferably in one dose.

Specific compounds and enantiomers are:

N-{1-[1-(4-Chlorophenyl)cyclobutyl]-3-methylbutyl}-N,N-dilrethyl-amine (known as sibutramine), especially as the hydrochloride-monohydrate salt (R)-N-{1-[1-(4-Cnlorophenyl)cyclobutyl]-3-methylbutyl}-N,N-dimethylamine, especially as the hydrochloride salt p1 (S)-N-{1-[1-(4-Chlorophenyl)cyclobutyl]-3-methylbutyl}-N,N-dimethylamine, especially as the hydrochloride salt N-{1-[1-(4-Chlorophenyl)cyclobutyl]-3-methylbutyl}-N-methyiamine, especially as the free base or as the hydrochloride salt (R)-N-{1-[1-(4-Chlorophenyl)cyclobutyl]-3-methylbutyl}-N-methylamine, especially as the free base or as the hydrochloride salt (S)-N-{1-[1-(4-Chlorophenyl)cyclobutyl]-3-methylbutyl}-N-methylamine, especially as the free base or as the hydrochloride salt N-{1-[1-(4-Chlorophenyl)cyclobutyl]-3-methylbutyl}amine, especially as the free base or as the hydrochloride salt (R)-N-{1-[1-(4-Chlorophenyl)cyclobutyl]-3-methylbutyl}amine, especially as the tree base or as the hydrochloride salt (S)-N-{1-[1-(4-Chlorophenyl)cyclobutyl]-3-methylbutyl}amine, especially as the free base or as the hydrochloride salt Tablets are e.g. produced from the following ingredients:

|  | Parts by weight |
|---|---|
| Active ingredient | 10.0 |
| Lactose | 78.5 |
| Polyvinylpyrrolidone | 5.0 |
| Corn starch | 15.0 |
| Magnesium stearate | 1.5 |

The active ingredient, the lactose and part of the starch are mixed and granulated with a solution of the polyvinylpyrrolidone in ethanol. The granules are mixed with the stearic acid and the remainder of the starch, and the mixture is compressed to tablets containing 10.0 mg of the active ingredient in a tabletting machine.

Capsules are produced in the following way: a mixture of the active ingredient (45 parts by weight) and lactose powder (205 parts by weight) is packed in hard gelatin capsules so that each capsule contains 2.5 mg of the active ingredient.

Tablets provided with a coating which dissolves only in the intestine are produced by coating the tablets with a thin layer of shellac lacquer, followed by 20 coatings of cellulose acetate phthalate, in a manner know to the skilled worker. The capsules can be provided with a coating which dissolves only in the intestine in a similar way.

Suppositories are produced by incorporating 10 parts by weight of the finely ground active ingredient in 1200 parts by weight of triglyceride suppository base, and the mixture is shaped to suppositories, each of which contains 10 mg of the active ingredient.

The compounds of the formula I are suitable for treating urinary incontinence, in particular urge incontinence, and especially stress incontinence.

The effect of the new compound was shown with sibutramine on volunteers suffering from urinary stress incontinence. At a daily dosage of 10 mg per day and person the incontinence syndrome nearly disappeared. Interrupting the drug treatment restored the condition to the state before the commencement of treatment.

I claim:

1. A method of treating urinary incontinence in humans which method comprises administering to a patient in need of such treatment an effective amount of an aryl-substituted cyclobutylalkylamine of formula I

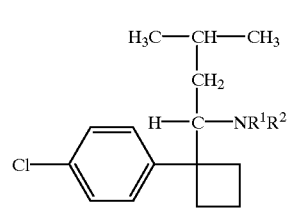

or an enantiomer thereof or a pharmaceutically acceptable salt thereof; where $R^1$ and $R^2$ are identical or different and are each hydrogen or methyl.

2. A method of treating urinary incontinence in humans which method comprises administering to a patient in need of such treatment an effective amount of sibutramine or an enantiomer thereof or a pharmaceutically acceptable salt thereof.

3. The method of claim 1, wherein the cyclobutylalkylamine of the formula I is N-{1-[1-(4-Chlorophenyl)cyclobutyl]-3-methylbutyl}-N,N-dimethylamine or the hydrochloride-monohydrate salt thereof.

4. The method of claim 1, wherein the cyclobutylalkylamine of the formula I is (R)-N-{1-[1-(4-Chlorophenyl)cyclobutyl]-3-methylbutyl}-N,N-dimethylamine or the hydrochloride salt thereof.

5. The method of claim 1, wherein the cyclobutylalkylamine of the formula I is (S)-N-{1-[1-(4-Chlorophenyl)cyclobutyl]-3-methylbutyl}-N,N-dimethylamine or the hydrochloride salt thereof.

6. The method of claim 1, wherein the cyclobutylalkylamine of the formula I is N-{1-[1-(4-Chlorophenyl)cyclobutyl]-3-methylbutyl}-N-methylamine or the hydrochloride salt thereof.

7. The method of claim 1, wherein the cyclobutylalkylamine of the formula I is (R)-N-{1-[1-(4-Chlorophenyl)cyclobutyl]-3-methylbutyl}-N-methylamine or the hydrochloride salt thereof.

8. The method of claim 1, wherein the cyclobutylalkylamine of the formula I is (S)-N-{1-[1-(4-Chlorophenyl)cyclobutyl]-3-methylbutyl}-N-methylamine or the hydrochloride salt thereof.

9. The method of claim 1, wherein the cyclobutylalkylamine of the formula I is N-{1-[1-(4-Chlorophenyl)cyclobutyl]-3-methylbutyl}-amine or the hydrochloride salt thereof.

10. The method of claim 1, wherein the cyclobutylalkylamine of the formula I is (R)-N-{1-[1-(4-Chlorophenyl)cyclobutyl]-3-methylbutyl}amine or the hydrochloride salt thereof.

11. The method of claim 1, wherein the cyclobutylalkylamine of the formula I is (S)-N-{1-[1-(4-Chlorophenyl)cyclobutyl]-3-methylbutyl}amine or the hydrochloride salt thereof.

12. The method of claim 1, wherein the cyclobutylalkylamine of the formula I is in a dextrorotatory form.

13. The method of claim 1, wherein the cyclobutylalkylamine of the formula I or the enantiomer thereof or the pharmaceutically acceptable salt thereof is administered in an amount of from 5 to 100 mg per day.

14. The method of claim 1, wherein the cyclobutylalkylamine of the formula I or the enantiomer thereof or the pharmaceutically acceptable salt thereof is administered in an amount of from 5 to 50 mg per day.

15. The method of claim 1, wherein the cyclobutylalkylamine of the formula I or the enantiomer thereof or the pharmaceutically acceptable salt thereof is administered in an amount of from 5 to 30 mg per day.

* * * * *